United States Patent [19]

Miller

[11] Patent Number: 5,614,635
[45] Date of Patent: Mar. 25, 1997

[54] METHOD FOR THE PREPARATION OF PYRIDINE-2,3-DICARBOXYLIC ACIDS

[75] Inventor: Paul E. Miller, Palmyra, Mo.

[73] Assignee: American Cyanamid Company, Madison, N.J.

[21] Appl. No.: 515,843

[22] Filed: Aug. 16, 1995

Related U.S. Application Data

[63] Continuation of Ser. No. 174,658, Dec. 28, 1993, abandoned.

[51] Int. Cl.$^6$ .................................................. C07D 213/807
[52] U.S. Cl. ........................... 546/320; 546/170; 546/321
[58] Field of Search ..................................... 546/170, 320, 546/321

[56] References Cited

U.S. PATENT DOCUMENTS

| | | | |
|---|---|---|---|
| 4,754,039 | 6/1988 | Michalowicz | 546/320 |
| 4,816,588 | 3/1989 | Rieker et al. | 546/321 |
| 5,281,713 | 1/1994 | Strong et al. | 546/179 |
| 5,334,576 | 8/1994 | Doehner, Jr. et al. | 504/128 |

FOREIGN PATENT DOCUMENTS

| | | |
|---|---|---|
| 0232118 | 8/1987 | European Pat. Off. . |
| 0388619 | 9/1990 | European Pat. Off. . |
| 1246260 | 2/1989 | Japan . |
| 2083370 | 3/1990 | Japan . |
| 3101661 | 4/1991 | Japan . |

*Primary Examiner*—Zinna Northington Davis
*Attorney, Agent, or Firm*—Charles F. Costello, Jr.

[57] ABSTRACT

The present invention provides an improved method for the preparation of pyridine-2,3-dicarboxylic acids by the continuous oxidation of substituted quinolines.

18 Claims, No Drawings

METHOD FOR THE PREPARATION OF PYRIDINE-2,3-DICARBOXYLIC ACIDS

This is a continuation of copending application(s) Ser. No. 08/174,658 filed on Dec. 28, 1993 now abandoned.
Statement

BACKGROUND OF THE INVENTION

The discovery, development and commercialization of the 2-(2-imidazolin-2-yl)pyridine compounds as herbicidal agents has given new meaning to the term "weed control"; for within this series of compounds it has been found that some are broad-spectrum or total vegetation herbicides with activity in both herbaceous and woody plants while others are highly selective weed control agents useful in the presence of crops.

Several methods for the preparation of herbicidal 2-(2-imidazolin-2-yl)pyridines involve the preparation of pyridine-2,3-dicarboxylic acid anhydrides from pyridine-2,3-dicarboxylic acids. Current methods used to prepare pyridine-2,3-dicarboxylic acids include the hydrogen peroxide-base oxidation of substituted quinolines (U.S. Pat. No. 4,816,588) and the sequential two part oxidation of substituted quinolines under basic conditions (EP-331,899A).

However, it has been found that those methods are not entirely satisfactory for the preparation of pyridine-2,3-dicarboxylic acids. The hydrogen peroxide-base oxidation is extremely exothermic and produces a large amount of foam to handle. In addition, that reaction may "hang-fire"—that is, accumulate a sizeable amount of unreacted reagents which then, suddenly, react all at once, releasing large amounts of heat and heavy foam. Such a reaction could lead to a rapid overpressurization of the vessel and explosive results. Many engineering and administrative safeguards are required to ensure that the reaction is proceeding in a controlled manner and that sufficient cooling and head space for foam are available. These issues present a significant obstacle in designing commercial scale reaction equipment.

A great amount of time and effort has gone into trying to develop a method for the oxidation of substituted quinolines which controls the rate of reaction and, consequently, the heat release and foaming, to what can be handled safely while, at the same time, minimizes reaction time. Conventional design techniques for running this reaction continuously were unsuccessful since the uneven reaction rate causes foaming and large heat releases to occur at irregular intervals causing significant variations in the reaction environment, temperature, and, therefore, flow rates and residence time. Conventional continuous reactor configurations, therefore, gave not only poor control of extent of reaction, but also can produce unsafe "hang-fire" conditions.

It is therefore an object of the present invention to provide a continuous method for the preparation of pyridine-2,3-dicarboxylic acids which minimizes the foam problems associated with the hydrogen peroxide-base oxidations of substituted quinolines.

SUMMARY OF THE INVENTION

The present invention relates to an improved method for the preparation of pyridine-2,3-dicarboxylic acids of formula I

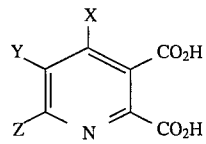

wherein
- X is hydrogen, or methyl, with the proviso that when Y and Z are taken together to form a ring in which YZ is represented by the structure: $—(CH_2)_n—$, where n is 3 or 4, X is hydrogen;
- Y is hydrogen, halogen, $C_1$–$C_6$alkyl, $C_1$–$C_6$hydroxyalkyl, $C_1$–$C_6$alkoxyalkyl, $C_1$–$C_6$haloalkyl, $C_1$–$C_6$aminoalkyl alkyl, $C_1$–$C_6$sulfonylalkyl, nitro, hydroxy, formyl, carboxy, acyl, amido, amino, $C_1$–$C_4$alkylamino, diloweralkylamino, $C_{b\ 1}$–$C_4$alkylsulfonyl, sulfonamido, or phenyl optionally substituted with one $C_1$–$C_4$alkyl group, $C_1$–$C_4$alkylsulfonyl group, halogen, hydroxy, or trifluoromethyl group;
- Z is hydrogen, $C_1$–$C_6$alkyl, $C_1$–$C_6$hydroxyalkyl, $C_1$–$C_6$halo alkyl, $C_1$–$C_6$aminoalkyl, $C_1$–$C_6$sulfonylalkyl nitro, hydroxy, formyl, carboxy, acyl, amido, amino, $C_1$–$C_4$alkylamino, diloweralkylamino, $C_1C_4$alkylsulfonyl, sulfonamido, or phenyl option substituted with one $C_1$–$C_4$alkyl group, $C_1C_4$alkylsulfonyl group, halogen, hydroxy, or trifluoromethyl group; and when taken together,
- Y and Z may form a ring in which YZ is represented by the structure: $—(CH_2)_n—$, where n is 3 or 4, provided that X is hydrogen; or

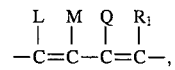

where L M, Q, and $R_1$ each represent members selected from the group consisting of hydroxy, halogen, $C_1$–$C_4$alkyl, $C_1$–$C_4$alkylsulfonyl, $C_1$–$C_4$haloalkylamino, $C_1$–$C_4$alkylamino, diloweralkylamino, and trifluoromethyl, with the proviso that only one of L, M, Q or $R_1$ may represent a substituent other than hydrogen, halogen, or $C_1$–$C_4$alkyl.

Said compounds and their use as intermediates in the preparation of herbicidal 2-(2-imidazolin-2-yl)-pyridines are described U.S. Pat. No. 4,518,780 and in commonly assigned, U.S. Pat. No. 5,335,576.

It has been found that the method of the present invention handles the heavy foaming, high heat release and "hang-fire" conditions in a more desirable way than the methods known in the art. Advantageously, the method of the present invention prepares formula I pyridine-2,3-dicarboxylic acids more safely, more economically and in a more environmentally friendly manner than the methods known in the art.

The method of the present invention comprises continuously oxidizing a substituted quinoline of formula II

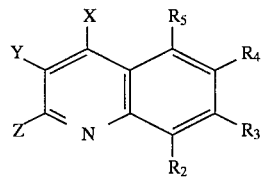

wherein
- X, Y, and Z are as described for formula I above, $R_2$, $R_3$, $R_4$ and $R_5$ are each independently hydrogen, hydroxy, $C_1$–$C_4$alkoxy, $SO_3H$, $SO_2C_1$, SH, halogen, $NO_2$ or NH$_2$; with the proviso that one of R$_2$, R$_3$, R$_4$ or R$_5$ is other than hydrogen;

the N-oxides thereof; and the acid addition salts thereof; by continuously adding aqueous hydrogen peroxide, aqueous base and the formula II substituted quinoline or a solution of the formula II substituted quinoline in aqueous mineral acid or a portion of the aqueous base to a first reaction vessel to form a reaction mixture, allowing the reaction mixture to foam over into a second reaction vessel to form an aqueous solution containing a formula I pyridine-2,3-dicarboxylic acid salt, removing the aqueous solution from the second reaction vessel, and adding mineral acid to the aqueous solution to form the desired pyridine-2,3dicarboxylic acid of formula I.

DETAILED DESCRIPTION OF THE INVENTION

The present invention provides an improved method for the preparation of pyridine-2,3-dicarboxylic acids of formula I

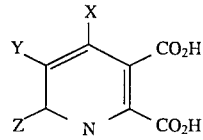

wherein X, Y and Z are as described for formula I above, which comprises continuously oxidizing a substituted quinoline of formula II

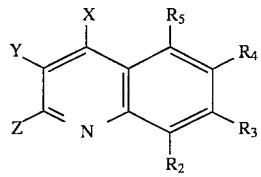

wherein

X, Y, and Z are as described for formula I above,

R$_2$, R$_3$, R$_4$ and R$_5$ are each independently hydrogen, hydroxy, C$_1$-C$_4$alkoxy, SO$_3$H, SO$_2$Cl, SH, halogen, NO$_2$ or NH$_2$; with the proviso that one of R$_2$, R$_3$, R$_4$ or R$_5$ is other than hydrogen;

the N-oxides thereof; and the acid addition salts thereof; by continuously adding aqueous hydrogen peroxide, aqueous base and the formula II substituted quinoline or a solution of the formula II substituted quinoline in aqueous mineral acid or a portion of the aqueous base to a first reaction vessel to form a reaction mixture, allowing the reaction mixture to foam over into a second reaction vessel to form an aqueous solution containing a formula I pyridine-2,3-dicarboxylic acid salt, removing the aqueous solution from the second reaction vessel, and adding mineral acid to the aqueous solution to form the desired pyridine-2,3-dicarboxylic acid of formula I.

Advantageously, it has been discovered that the foam problems associated with the art methods are controlled by allowing the reaction mixture to continuously foam over into a second reaction vessel. Surprisingly, the present invention provides an efficient method for the conversion of formula II substituted quinolines to formula I pyridine-2,3-dicarboxylic acids without controlling residence time in the first reaction vessel.

Aqueous bases suitable for use in the method of the invention include alkali metal and alkaline earth metal hydroxides and carbonates such as sodium, potassium, lithium, and calcium hydroxides or carbonates and mixtures thereof. Aqueous sodium hydroxide and aqueous potassium hydroxide are the preferred aqueous bases. In general, base concentrations of 10% to 50% on a weight basis and hydrogen peroxide concentrations of 30% to 50% on a weight basis are preferred.

The method of the present invention preferably comprises adding 8 to 20 molar equivalents of hydrogen peroxide and 5 to 10 molar equivalents of base per mole of the formula II substituted quinoline. The aqueous hydrogen peroxide, aqueous base and formula II substituted quinoline are preferably added to the first reaction vessel in separate streams. The first reaction vessel preferably contains an initial charge of water, dilute aqueous base or aqueous solution from a previous run. Additional water may be continuously added to the first reaction vessel. The formula II substituted quinoline is preferably added to the first reaction vessel in a liquid state.

In the method of the present invention, the temperature of the reaction mixture in the first reaction vessel is preferably about 80° to 120° C. and most preferably about 95° to 110° C. The temperature of the aqueous solution in the second reaction vessel is preferably about 60° to 120° C. and most preferably about 90° to 110° C.

The present invention is especially useful for the preparation of formula I pyridine-2,3-dicarboxylic acids wherein X and Z are hydrogen; and Y is hydrogen, C$_1$-C$_6$alkyl or C$_1$-C$_6$alkoxyalkyl.

Preferred starting formula II substituted quinolines are those wherein

X, Z, R$_3$, R$_4$ and R$_5$ are hydrogen;

Y is hydrogen, C$_1$-C$_6$alkyl or C$_1$-C$_6$alkoxyalkyl; and

R$_2$ is hydroxy, halogen, SO$_3$H, SO$_2$Cl, SH, NO$_2$ or NH$_2$.

Mineral acids suitable for use in the method of the present invention include sulfuric acid, hydrochloric acid, hydrobromic acid and phosphoric acid with sulfuric acid and hydrochloric acid being preferred.

The product formula I compounds may be isolated by conventional techniques such as filtration or extraction into a suitable solvent or solvent mixture.

Certain starting formula II substituted quinolines are described in U.S. Pat. No. 4,816,588 and allowed U.S. patent application Ser. No. 07/961,471, filed on Oct. 23, 1992, now U.S. Pat. No. 5,281,713.

In order to facilitate a further understanding of the invention, the following examples are presented to illustrate more specific details thereof. The invention is not to be limited thereby except as defined in the claims.

EXAMPLE 1

Continuous oxidation of 3-Ethyl-8-hydroxyquinoline to 5-Ethylpyridine-2,3-dicarboxylic acid An aqueous solution (51 g) from a previous preparation containing 10.7 wt/wt % 5-ethylpyridine-2,3dicarboxylic acid, disodium salt is charged to a 100 mL reactor vessel. The starting charge is heated to 100° C. and 35 wt/wt % aqueous hydrogen peroxide (797 g, 8.2 mol), 50 wt/wt % aqueous sodium hydroxide (337 g, 4.2 mol) and molten 3-ethyl-8-hydroxyquinoline (95% real, 111 g, 0.609 mol) are added in separate streams at 4.7 g/minute, 2.0 g/minute and 0.65 g/minute, respectively, to the stirred reaction vessel. The reaction mixture is allowed to foam over into a stirred, 1,000 mL second reaction vessel to form an aqueous solution which is maintained at 90° –100° C. A portion of the aqueous solution is removed from the second reaction vessel and stored in a receiver. When all of the reactants are added, the first reaction vessel, second reaction vessel and receiver are assayed and found to contain 105.8 g, 89% yield of 5-ethyl-pyridine-2,3-dicarboxylic acid after adjusting the total to remove the starting charge. Sulfuric acid is then added to the aqueous solution in the receiver to obtain the title product.

Using essentially the same procedure, but substituting 3-methyl-8-hydroxyquinoline and 8-hydroxyquinoline for 3-ethyl-8-hydroxyquinoline, 5methyl-pyridine-2,3-dicarboxylic acid and pyridine-2,3-dicarboxylic acid are obtained, respectively. 32,357

I claim:

1. A method for the preparation of a pyridine-2,3-dicarboxylic acid of formula I

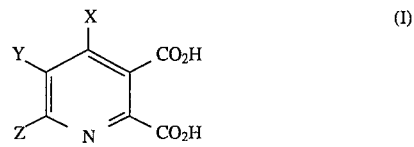

Wherein

X is hydrogen, or methyl, with the proviso that when Y and Z are taken together to form a ring in which YZ is represented by the structure: —$(CH_2)_n$—, where n is 3 or 4, X is hydrogen;

Y is hydrogen, halogen, $C_1$–$C_6$alkyl, $C_1$–$C_6$hydroxyalkyl, $C_1$–$C_6$alkoxyalkyl, $C_1$–$C_6$haloalkyl, $C_1$–$C_6$aminoalkyl $C_1$–$C_6$sulfonylalkyl, nitro, hydroxy, formyl, carboxy, acyl, amido, amino, $C_1$–$C_4$alkylamino diloweralkylamino, $C_1$–$C_4$alkyl sulfonyl, sulfonamido, or phenyl optionally substituted with one $C_1$–$C_4$alkyl group, $C_1$–$C_4$alkylsulfonyl group, halogen, hydroxy, or trifluoromethyl group;

Z is hydrogen, $C_1$–$C_6$alkyl, $C_1$–$C_6$hydroxyalkyl, $C_1$–$C_6$halo-alkyl $C_1$–$C_6$aminoalkyl, $C_1$–$C_6$sulfonylalkyl, nitro, hydroxy, formyl, carboxy, acyl, amido, amino, $C_1$–$C_4$-alkylamino, diloweralkylamino, $C_1$–$C_4$alkylsulfonyl, sulfonamido, or phenyl optionally substituted with one $C_1$–$C_4$alkyl group, $C_1$–$C_4$alkylsulfonyl group, halogen, hydroxy, or trifluoromethyl group; and when taken together, Y and Z may form a ring in which YZ is represented by the structure: —$(CH_2)_n$—, where n is 3 or 4, provided that X is hydrogen; or

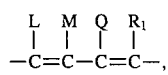

where L, M, Q, and $R_1$ each represent members selected from the group consisting of hydroxy, halogen, $C_1$–$C_4$alkyl, $C_1$–$C_4$alkyl sulfonyl, $C_1$–$C_4$haloalkylamino, $C_1$–$C_4$alkylamino, diloweralkylamino, and trifluoromethyl, with the proviso that only one of L, M, Q or $R_1$ may represent a substituent other than hydrogen, halogen, or $C_1$–$C_4$alkyl, which comprises continuously oxidizing a substituted quinoline of formula II

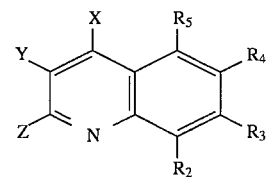

wherein

X, Y, and Z are as described for formula I above, $R_2$, $R_3$, $R_4$ and $R_5$ are each independently hydrogen, hydroxy, $C_1$–$C_4$alkoxy, $SO_3H$, $SO_2Cl$, SH, halogen, $NO_2$ or $NH_2$; with the proviso that one of $R_2$, R3, $R_4$ or $R_5$ is other than hydrogen;

the N-oxides thereof; and the acid addition salts thereof; by continuously adding aqueous hydrogen peroxide, aqueous base and the formula II substituted quinoline or a solution of the formula II substituted quinoline in aqueous mineral acid or a portion of the aqueous base to a first reaction vessel to form a reaction mixture, allowing the reaction mixture to foam over into a second reaction vessel to form an aqueous solution containing a formula I pyridine-2,3-dicarboxylic acid salt, removing the aqueous solution from the second reaction vessel, and adding mineral acid to the aqueous solution to form the desired pyridine-2,3-dicarboxylic acid of formula I.

2. The method according to claim 1 wherein 8 to 20 molar equivalents of hydrogen peroxide and 5 to 10 molar equivalents of base are added per mole of the formula II substituted quinoline.

3. The method according to claim 1 wherein the aqueous hydrogen peroxide contains about 30% to 50% hydrogen peroxide on a weight basis.

4. The method according to claim 1 wherein the aqueous base contains about 10% to 50% base on a weight basis.

5. The method according to claim 1 wherein the base is selected from the group consisting of an alkali metal hydroxide, an alkaline earth metal hydroxide, an alkali metal carbonate and an alkaline earth metal carbonate.

6. The method according to claim 5 wherein the base is selected from the group consisting of sodium hydroxide and potassium hydroxide.

7. The method according to claim 1 wherein the temperature of the reaction mixture in the first reaction vessel is about 80° to 120° C.

8. The method according to claim 7 wherein the temperature is about 95° to 110° C.

9. The method according to claim 1 wherein the temperature of the aqueous solution in the second reaction vessel is about 60° to 120° C.

10. The method according to claim 9 wherein the temperature is about 90° to 110° C.

11. The method according to claim 1 wherein the formula II substituted quinoline is added to the first reaction vessel in a liquid state.

12. The method according to claim 1 wherein the mineral acid is selected from the group consisting of sulfuric acid, hydrochloric acid, hydrobromic acid and phosphoric acid.

13. The method according to claim 12 wherein the mineral acid is selected from the group consisting of sulfuric acid and hydrochloric acid.

14. The method according to claim 1 for the preparation of a formula I pyridine-2,3-dicarboxylic acid wherein X and Z are hydrogen, and Y is hydrogen, $C_1$–$C_6$-alkyl or $C_1$–$C_6$alkoxyalkyl, from the appropriately substituted formula II substituted quinoline wherein X, Z, $R_3$, $R_4$ and $R_5$ are hydrogen, and $R_2$ is hydroxy, halogen, $SO_3H$, $SO_2Cl$, SH, $NO_2$ or $NH_2$; the N-oxides thereof or the acid addition salts thereof.

15. The method according to claim 14 wherein $R_2$ is hydroxy.

16. The method according to claim 15 for the preparation of 5-ethylpyridine-2,3-dicarboxylic acid from 3-ethyl-8-hydroxyquinoline or the acid addition salt thereof.

17. The method according to claim 15 for the preparation of 5-methylpyridine-2,3-dicarboxylic acid from 3-methyl-8-hydroxyquinoline or the acid addition salt thereof.

18. The method according to claim 15 for the preparation of pyridine-2,3-dicarboxylic acid from 8-hydroxyquinoline or the acid addition salt thereof.

* * * * *